US012700494B2

(12) United States Patent
Iwamura et al.

(10) Patent No.: US 12,700,494 B2
(45) Date of Patent: Aug. 4, 2026

(54) MEDICAL INFORMATION PROCESSING DEVICE, MEDICAL INFORMATION PROCESSING METHOD, AND STORAGE MEDIUM

(71) Applicant: Canon Kabushiki Kaisha, Tokyo (JP)

(72) Inventors: Taisuke Iwamura, Utsunomiya (JP);
Junichi Takazawa, Nasushiobara (JP);
Yuki Matsumoto, Utsunomiya (JP);
Satoshi Sugisawa, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 511 days.

(21) Appl. No.: 18/180,242

(22) Filed: Mar. 8, 2023

(65) Prior Publication Data

US 2023/0290486 A1     Sep. 14, 2023

(30) Foreign Application Priority Data

Mar. 11, 2022     (JP) ................................. 2022-038063

(51) Int. Cl.
*G16H 30/40*         (2018.01)
*G16H 30/20*         (2018.01)
*G16H 50/20*         (2018.01)

(52) U.S. Cl.
CPC ............. *G16H 30/40* (2018.01); *G16H 30/20* (2018.01); *G06T 2207/10* (2013.01); *G16H 50/20* (2018.01)

(58) Field of Classification Search
CPC ....................................................... G06T 11/60
See application file for complete search history.

(56) References Cited

U.S. PATENT DOCUMENTS

| | | | | |
|---|---|---|---|---|
| 2013/0308825 A1* | 11/2013 | Yamazaki | ................ | H04N 7/18 |
| | | | | 382/103 |
| 2014/0321726 A1* | 10/2014 | Shin | .......................... | G06T 7/32 |
| | | | | 382/131 |
| 2017/0262296 A1* | 9/2017 | Sohn | ....................... | H04L 67/51 |
| 2021/0157555 A1* | 5/2021 | Jiang | ......................... | G06F 8/38 |
| 2021/0210206 A1 | 7/2021 | Yamada | | |

FOREIGN PATENT DOCUMENTS

| | | | | | |
|---|---|---|---|---|---|
| CN | 103536305 A | * | 1/2014 | ............. | G16H 30/40 |
| WO | WO-2019188886 A1 | * | 10/2019 | ............. | G08G 1/137 |
| WO | WO 2020/066132 A1 | | 4/2020 | | |

* cited by examiner

*Primary Examiner* — Di Xiao

(74) *Attorney, Agent, or Firm* — Oblon, McClelland, Maier & Neustadt, L.L.P.

(57) ABSTRACT

A medical information processing device of an embodiment includes processing circuitry. The processing circuitry is configured to automatically select and execute an application to be executed on a medical image to be processed from among a plurality of applications on the basis of predetermined reference information, compare first information indicating execution conditions for each of the plurality of applications included in the reference information with second information indicating an imaging condition for the medical image, and cause a display to display a list of applications that have not been executed among the plurality of applications and a result of comparison between the first information and the second information.

8 Claims, 8 Drawing Sheets

| APPLICATION | MODALITY | EXAMINATION SITE | TAG | | |
| | | | CONTRAST MEDIUM | PROTOCOL NUMBER | ... |
|---|---|---|---|---|---|
| FIRST APPLICATION | CT | HEAD | - | - | - |
| SECOND APPLICATION | CT | - | Not Null | - | - |
| THIRD APPLICATION | MRI | BODY | - | - | - |
| FOURTH APPLICATION | US | UTERUS | - | - | - |
| ... | ... | ... | ... | ... | ... |

| APPLICATION | TAG | | | | |
|---|---|---|---|---|---|
| | MODALITY | EXAMINATION SITE | CONTRAST MEDIUM | PROTOCOL NUMBER | ⋮ |
| FIRST APPLICATION | CT | HEAD/NECK | – | – | – |
| SECOND APPLICATION | CT | – | Not Null | – | – |
| THIRD APPLICATION | MRI | BODY | – | – | – |
| FOURTH APPLICATION | US | UTERUS | – | – | – |
| ⋮ | ⋮ | ⋮ | ⋮ | ⋮ | ⋮ |

MEDICAL INFORMATION PROCESSING DEVICE, MEDICAL INFORMATION PROCESSING METHOD, AND STORAGE MEDIUM

CROSS-REFERENCE TO RELATED APPLICATION

The present application claims priority based on Japanese Patent Application No. 2022-038063 filed Mar. 11, 2022, the content of which is incorporated herein by reference.

FIELD

Embodiments disclosed in this specification and drawings relate to a medical information processing device, a medical information processing method, and a storage medium.

BACKGROUND

In recent years, in the field of medical image diagnosis, the development of technology using artificial intelligence (AI) functions has been progressing, and various AI applications according to purposes have been supplied by vendors. These AI applications execute various analyses and computations on behalf of doctors and the like. Medical institutions can improve the efficiency of medical practice by introducing such AI applications.

In addition, along with the progress of the aforementioned AI applications, the development of a platform for executing AI applications (hereinafter also referred to as "AI platform") has also been underway. One important function in an AI platform is a "rule engine" that determines which AI application will be executed on an image to be analyzed. For example, in the case of images conforming to Digital Imaging and Communication in Medicine (DICOM) standard, the rule engine automatically selects and executes an AI application suitable for the images using incidental information such as DICOM tags.

In the AI platform as described above, the AI application is not executed unless the incidental information of the images matches a rule predetermined in the rule engine. Therefore, a desired AI application may not be executed on an image to be analyzed, contrary to expectation of the user of the AI platform. In this case, the user cannot ascertain the cause of non-execution of the AI application.

BRIEF DESCRIPTION OF THE DRAWINGS

FIG. 2 is a diagram showing an example of a data configuration of a rule RL according to the embodiment.

FIG. 7 is a flowchart showing an example of a flow of rule update processing of the medical information processing device 1 according to the embodiment.

FIG. 8 is a diagram showing an example of a data configuration after update of the rule RL according to the embodiment.

DETAILED DESCRIPTION

A medical information processing device, a medical information processing method, and a storage medium according to embodiments will be described below with reference to the drawings.

A medical information processing device of an embodiment includes processing circuitry. The processing circuitry is configured to automatically select and execute an application to be executed on a medical image to be processed from among a plurality of applications on the basis of predetermined reference information, compare first information indicating execution conditions for each of the plurality of applications included in the reference information with second information indicating an imaging condition for the medical image, and cause a display to display a list of applications that have not been executed among the plurality of applications and a result of comparison between the first information and the second information. According to the medical information processing device of the embodiment, it is possible to provide information related to execution of applications.

[Configuration of Medical Information Processing Device]

Figure 1:
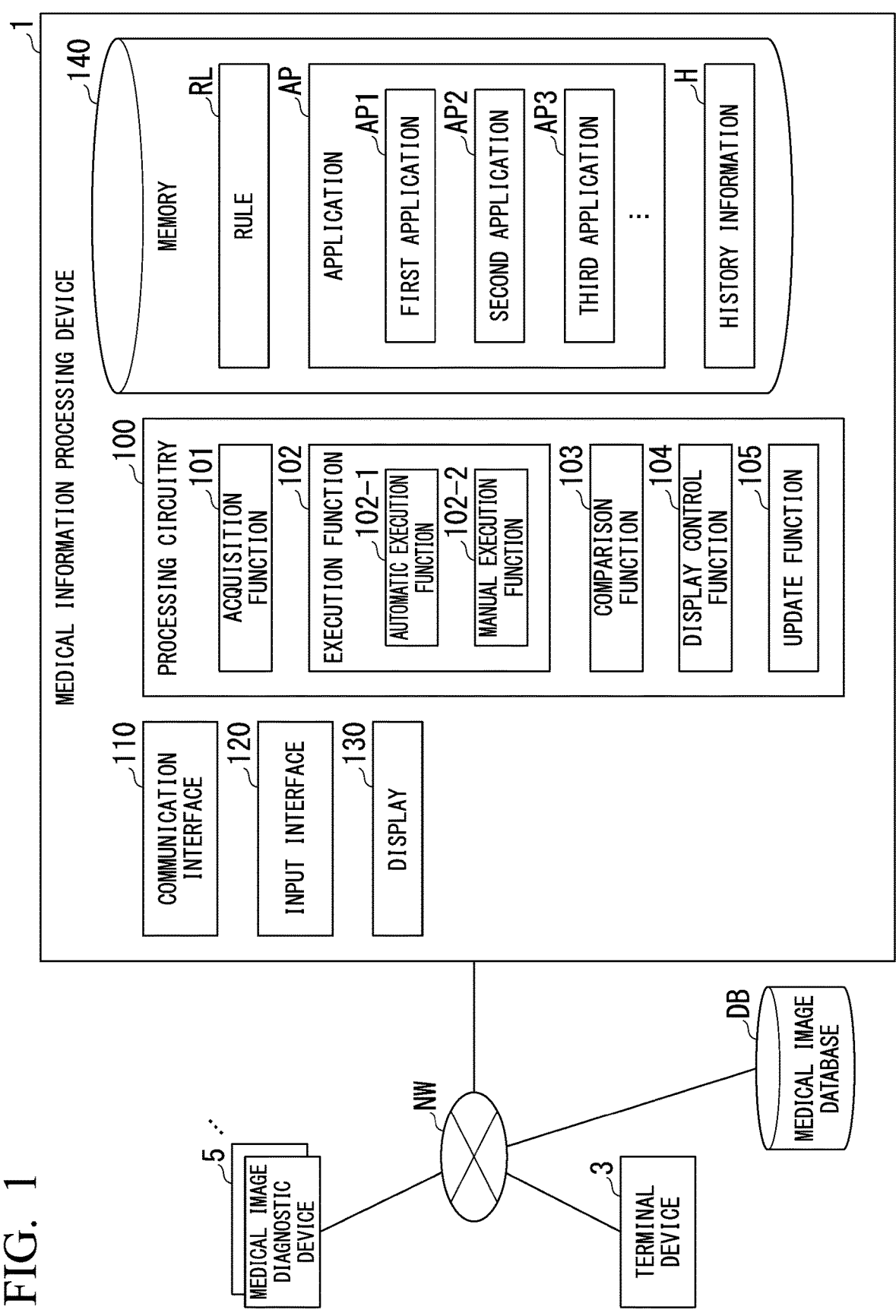
FIG. 1 is a diagram showing an example of a usage environment and functional blocks of a medical information processing device 1 according to an embodiment.

FIG. 1 is a diagram showing an example of a usage environment and functional blocks of a medical information processing device 1 according to an embodiment. The medical information processing device 1 provides functions of an AI platform that executes applications. The applications perform various types of analysis processing according to purposes on a medical image to be analyzed. The applications include, for example, clinical applications for detecting lesions of patients, applications for site segmentation, applications for checking tumors, applications for determining progression of lesions, applications for detecting the location of a specific lesion such as cerebral infarction, and the like. An application is, for example, a machine learning model generated by learning processing using a machine learning technique such as deep learning.

The medical information processing device 1 is provided, for example, in a medical institution such as a hospital. The medical information processing device 1 may be, for example, a workstation, a server, or the like. The medical information processing device 1 is connected to, for example, at least one terminal device 3, at least one medical image diagnostic device 5, a medical image database DB, and the like via a communication network NW such that data can be transmitted and received.

The communication network NW indicates general information communication networks using telecommunication technology. The communication network NW includes a telephone communication network, an optical fiber communication network, a cable communication network, a satellite communication network, and the like in addition to a wireless/wired local area network (LAN) such as a hospital backbone LAN, and the Internet network.

The terminal device 3 is a device for using the functions of the AI platform provided by the medical information processing device 1. The terminal device 3 is, for example, a personal computer, a mobile terminal such as a tablet, a smartphone, or the like. The terminal device 3 is operated by, for example, a doctor, an engineer, or the like. The terminal device 3 activates a dedicated application program, a browser, or the like to provide various types of information provided by the medical information processing device 1 to a doctor or the like.

The medical image diagnostic device 5 images a patient (subject) to be diagnosed and generates a medical image. The medical image diagnostic device 5 is, for example, a modality such as an X-ray computed tomography (CT) apparatus, an X-ray diagnostic apparatus, a magnetic resonance imaging apparatus, an ultrasonic diagnostic apparatus, or a nuclear medicine diagnostic apparatus. The medical image diagnostic device 5 generates images having incidental information added thereto. The medical image diagnostic device 5 generates, for example, an image conforming to the DICOM standard (hereinafter referred to as a "DICOM image"). A DICOM tag (hereinafter simply referred to as a "tag") is attached to a DICOM image as incidental information. The tag includes, for example, a device ID that identifies each device (modality), an examination site, presence or absence of a contrast medium, a protocol number of imaging, a patient ID that identifies a patient, an examination ID that identifies an examination, information on a facility in which the apparatus is provided, an apparatus maker, or information manually input by an apparatus operator (engineer or the like).

The medical image database DB stores various images generated by the medical image diagnostic device 5. The medical image database DB stores, for example, CT images, magnetic resonance (MR) images, ultrasonic images, and the like for each patient. The medical image database DB is realized by, for example, a semiconductor memory element such as a random access memory (RAM) or a flash memory, a hard disk, or an optical disc.

The medical information processing device 1 includes, for example, processing circuitry 100, a communication interface 110, an input interface 120, a display 130, and a memory 140. The communication interface 110 communicates with external devices such as the terminal device 3, the medical image diagnostic device 5, and the medical image database DB via the communication network NW. The communication interface 110 includes, for example, a communication interface such as a network interface card (NIC).

The input interface 120 receives various input operations from the operator of the medical information processing device 1, converts the received input operations into electrical signals, and outputs the electrical signals to the processing circuitry 100. For example, the input interface 120 includes a mouse, a keyboard, a trackball, a switch, a button, a joystick, a touch panel, and the like. The input interface 120 may be, for example, a user interface that receives voice input such as a microphone.

The input interface in this specification is not limited to one having physical operation parts such as a mouse and a keyboard. For example, the input interface also includes electrical signal processing circuitry that receives an electrical signal corresponding to an input operation from an external input device provided separately from the apparatus and outputs the electrical signal to a control circuit.

The display 130 displays various types of information. For example, the display 130 displays an image generated by the processing circuitry 100, a graphical user interface (GUI) for receiving various input operations from the operator, and the like. For example, the display 130 is a liquid crystal display (LCD), a cathode ray tube (CRT) display, an organic electroluminescence (EL) display, or the like.

The processing circuitry 100 includes, for example, an acquisition function 101, an execution function 102, a comparison function 103, a display control function 104, and an update function 105. The processing circuitry 100 realizes these functions by, for example, a hardware processor (computer) executing a program stored in the memory 140 (storage circuit).

The hardware processor is, for example, circuitry such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). The program may be configured to be directly embedded in the circuit of the hardware processor instead of being stored in the memory 140. In this case, the hardware processor realizes the functions by reading and executing the program embedded in the circuit. The aforementioned program may be stored in the memory 140 in advance, or may be stored in a non-transitory storage medium such as a DVD or CD-ROM and installed in the memory 140 from the non-transitory storage medium when the non-transitory storage medium is set in a drive device (not shown) of the medical information processing device 1. The hardware processor is not limited to being configured as a single circuit, and may be configured as one hardware processor by combining a plurality of independent circuits to realize each function. Further, a plurality of components may be integrated into one hardware processor to realize each function.

The acquisition function 101 acquires medical image data from the medical image database DB and the medical image diagnostic device 5 via the communication network NW.

The execution function 102 includes, for example, an automatic execution function 102-1 and a manual execution function 102-2. The automatic execution function 102-1 automatically selects and executes an application for a medical image to be analyzed using a rule engine in response to a request from the terminal device 3. The automatic execution function 102-1 automatically selects and executes an application on the basis of a rule RL (reference information) stored in the memory 140. The manual execution function 102-2 executes an application manually designated by a user (doctor or the like) of the terminal device 3 on a medical image to be analyzed in response to a request from the terminal device 3. The execution function 102 is an example of an "executor." That is, the execution function 102 automatically selects and executes an application to be executed on a medical image to be processed from among a plurality of applications on the basis of predetermined reference information. The execution function 102 also executes an application manually designated by the user on a medical image.

The comparison function 103 compares setting information (execution conditions, first information) predetermined in the rule RL with incidental information (examination information, second information) provided to a medical image to be analyzed and indicating imaging conditions for medical images, and determines whether the setting information and the incidental information match. The comparison function 103 is an example of a "comparator." That is, the comparison function 103 compares the first information indicating execution conditions for each of the plurality of applications included in the reference information with the second information indicating the imaging conditions for medical images.

The display control function 104 generates information for various pages on the basis of processing results of an application executed by the execution function 102 and the comparison result obtained by the comparison function 103, and transmits the information to the terminal device 3. The display control function 104 is an example of a "display controller." That is, the display control function 104 causes a display to display a list of applications that have not been executed among the plurality of applications and the result of comparison between the first information and the second information. The display control function 104 causes the display to display the reason why the unexecuted application has not been executed. The display control function 104 causes the display to display information indicating differences between the first information and the second information.

The update function 105 performs processing of updating the rule RL. Details of update processing performed by the update function 105 will be described later. The update function 105 is an example of an "updater."

The memory 140 is realized by, for example, a semiconductor memory element such as a RAM or a flash memory, a hard disk, or an optical disc. These non-transitory storage media may be realized by other storage devices such as a network attached storage (NAS) and an external storage server device connected via the communication network NW. The memory 140 may also include non-transitory storage media such as a read only memory (ROM) and a register. The memory 140 stores, for example, the rule RL, applications AP, history information H, and the like. The applications AP include a first application AP1, a second application AP2, a third application AP3, and the like which perform various types of analysis processing according to purposes. In addition, the memory 140 stores programs, parameter data, and other data used by the processing circuitry 100.

FIG. 2 is a diagram showing an example of a data configuration of the rule RL. As shown in FIG. 2, in the rule RL, each condition for executing an application is defined in a tag format for each application. For example, for the "first application," it is defined as execution conditions for the application that a "modality" tag is "CT" and an "examination site" tag is "HEAD."

The history information H records a history when each application has been executed by the manual execution function 102-2 on the basis of an instruction by the user (doctor or the like) of the terminal device 3. This history information H is referenced by the update function 105. Details of the history information H will be described later.

[Processing Flow]

(Automatic Application Execution Processing)

Figure 3:
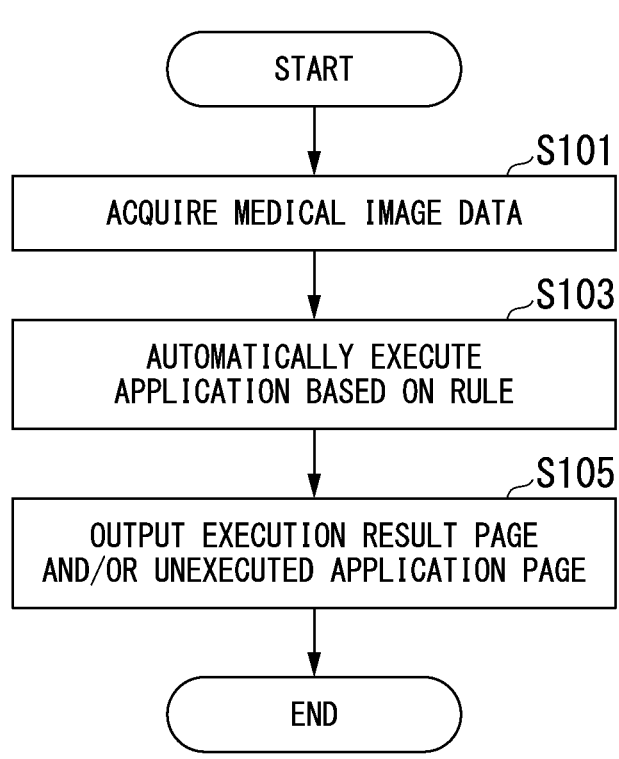
FIG. 3 is a flowchart showing an example of a flow of automatic application execution processing of the medical information processing device 1 according to the embodiment.

Next, various types of processing of the medical information processing device 1 according to the embodiment will be described. First, automatic application execution processing of the medical information processing device 1 will be described. FIG. 3 is a flowchart showing an example of a flow of automatic application execution processing of the medical information processing device 1. The automatic application execution processing shown in FIG. 3 is executed, for example, when the medical information processing device 1 receives a processing request transmitted from the terminal device 3 on the basis of an operation by a doctor or the like.

First, the acquisition function 101 acquires medical image data of a patient to be analyzed from the medical image database DB in response to the processing request from the terminal device 3 (step S101). The acquisition function 101 acquires the medical image data from the medical image database DB, for example, on the basis of a patient ID included in the processing request.

Next, the automatic execution function 102-1 automatically selects and executes an application corresponding to the acquired medical image data on the basis of the rule RL stored in the memory 140 (step S103). For example, the automatic execution function 102-1 compares examination information of a medical image to be analyzed with setting information predetermined in the rule RL stored in the memory 140, and automatically selects and executes an application having setting information matching the examination information of the medical image.

Next, the display control function 104 generates information for displaying an execution result page showing a result of execution of the application and/or an unexecuted application page showing an unexecuted application, and outputs the information to the terminal device 3 (step S105). The application execution result page displays, for example, information on a lesion of the patient detected by a clinical application.

Figure 4:
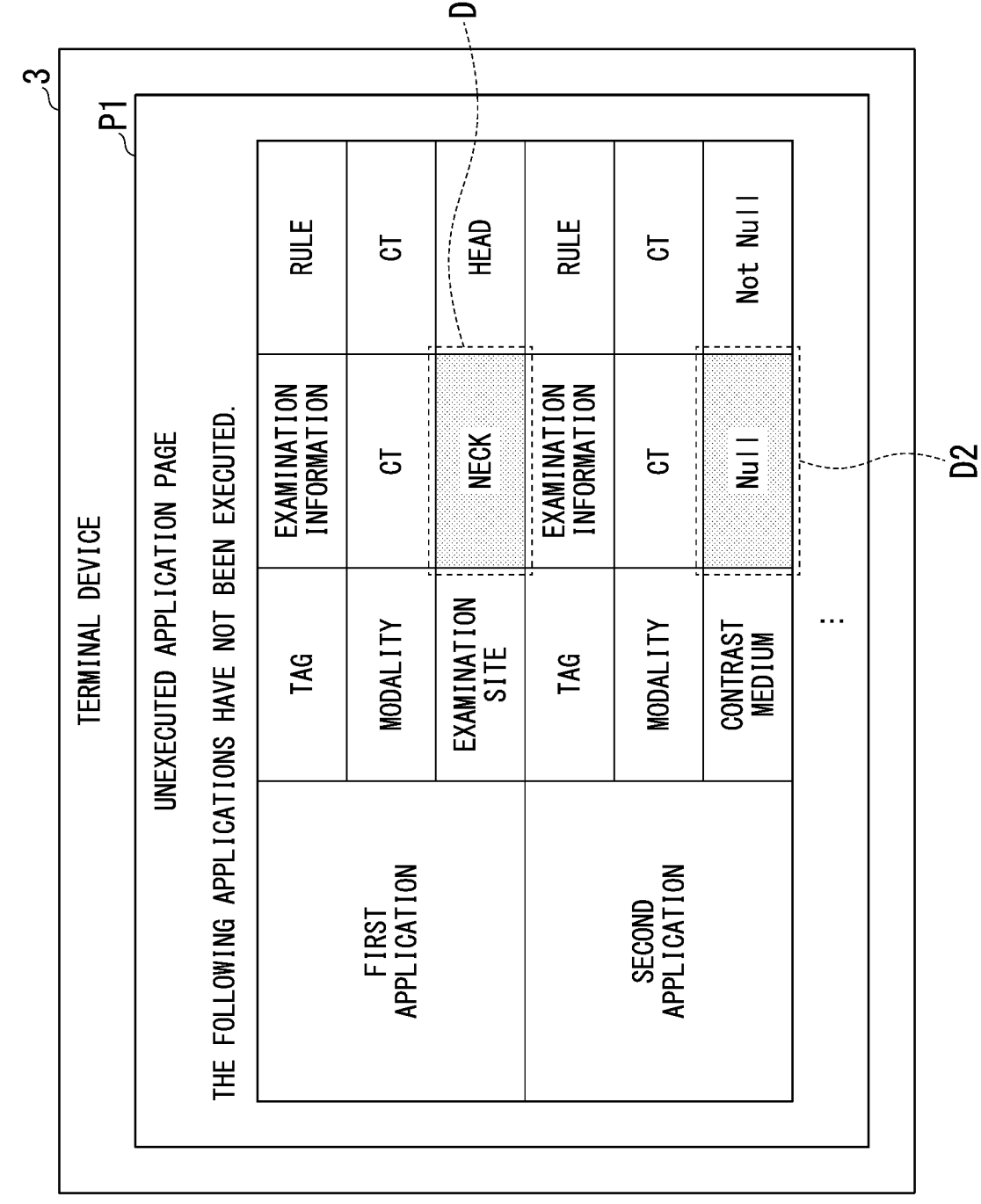
FIG. 4 is a diagram showing an example of an unexecuted application page P1 according to the embodiment.

FIG. 4 is a diagram showing an example of an unexecuted application page P1 displayed on the display of the terminal device 3. In the example shown in FIG. 4, a "first application" and a "second application" are displayed as unexecuted applications. In this unexecuted application page P1, a comparison result obtained by the comparison function 103 is displayed for each application.

In FIG. 4, with respect to the "first application," it is defined as execution conditions for the application that the "modality" tag is "CT" and the "examination site" tag is "HEAD" on the rule RL, whereas the "modality" tag is "CT" and the "examination site" tag is "NECK" in examination information of medical image data to be analyzed." In this case, the content ("CT") of both tags matches for the "modality" tag, but the content of both tags is different for the "examination site" tag. As shown in a part D1 in FIG. 4, the difference between the tags is highlighted. By referring to the unexecuted application page P1, the doctor or the like can ascertain that the first application has not been executed due to the difference in the content of the "examination site" tag.

In FIG. 4, with respect to the "second application," it is defined as execution conditions for the application that the "modality" tag is "CT" and a "contrast medium" tag is "Not Null (that is, there is a contrast medium)" on the rule RL, whereas the "modality" tag is "CT" and the "contrast medium" tag is "Null (that is, there is no contrast medium)" in the examination information of the medical image data to be analyzed. In this case, although the content ("CT") of both tags matches for the "modality" tag, the content of the "contrast medium" tag is different. As shown in a part D2 in FIG. 4, the difference between the tags is highlighted. By referring to the unexecuted application page P1, the doctor or the like can ascertain that the second application has not been executed due to the difference in the content of the "contrast medium" tag.

By checking the unexecuted application page P1 displayed on the terminal device 3 (checking highlighting of differences), the doctor or the like can ascertain the cause of non-execution of each application. Any display method may be used for highlighting. Highlighting includes, for example, changing and displaying characters of or a background color of a difference, enlarging and displaying characters of a difference, blinking and displaying characters of a difference, and the like. Accordingly, processing of this flowchart ends.

(Manual Application Execution Processing)

Figure 5:
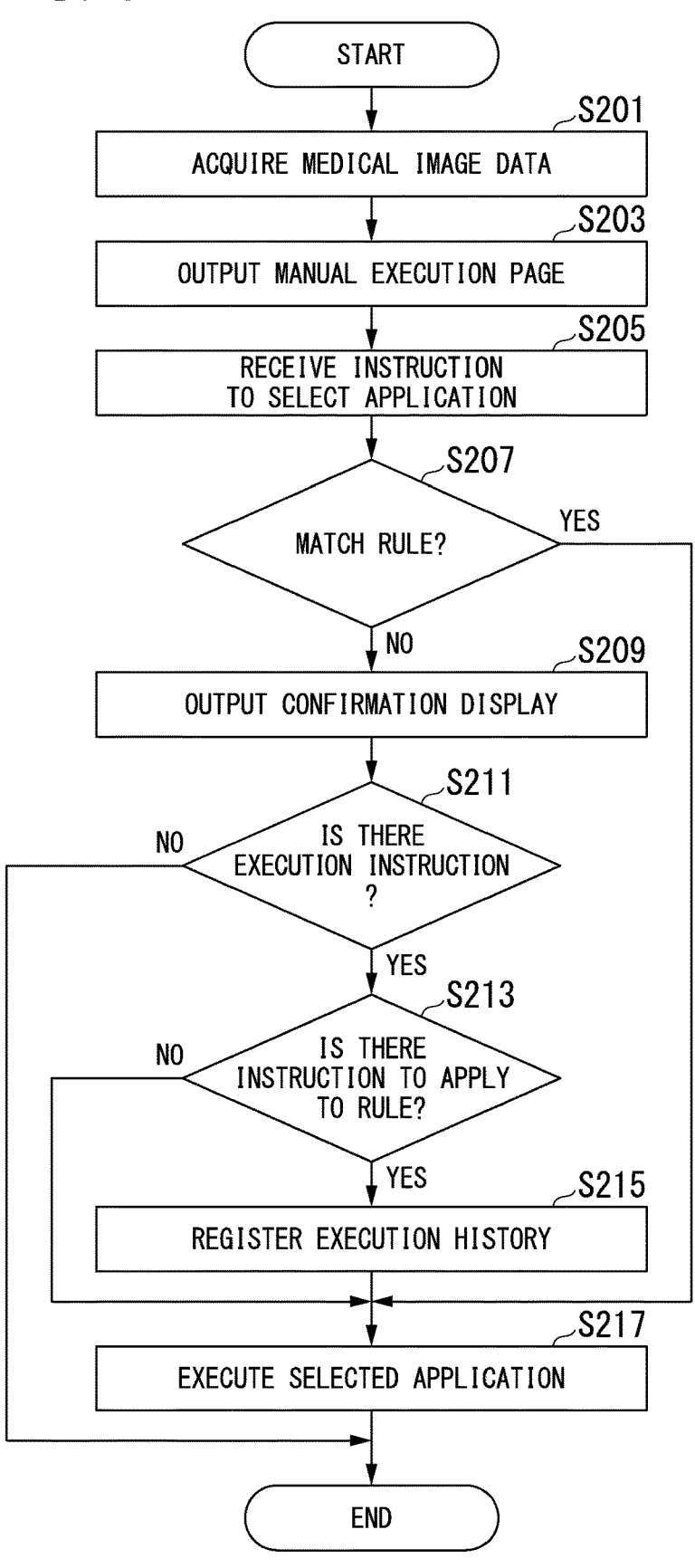
FIG. 5 is a flowchart showing an example of a flow of manual application execution processing of the medical information processing device 1 according to the embodiment.

Next, manual application execution processing of the medical information processing device 1 will be described. FIG. 5 is a flowchart showing an example of a flow of manual application execution processing of the medical information processing device 1. For example, when a desired application is not automatically executed, a doctor or the like can manually execute a designated application. The manual application execution processing shown in FIG. 5 is executed, for example, when the medical information processing device 1 receives a processing request transmitted from the terminal device 3 on the basis of an operation of the doctor or the like.

First, the acquisition function 101 acquires medical image data of a patient to be analyzed from the medical image database DB in response to the processing request from the terminal device 3 (step S201). The acquisition function 101 acquires the medical image data from the medical image database DB, for example, on the basis of a patient ID included in the processing request.

Next, the display control function 104 generates information of a manual execution page for receiving an instruction regarding manual execution and outputs the information to the terminal device 3 (step S203). The terminal device 3 displays the manual execution page on the display on the basis of the received information of the manual execution page. The doctor or the like can manually designate a medical image to be analyzed and an application to be executed on the medical image on the manual execution page displayed on the terminal device 3.

Figure 6:
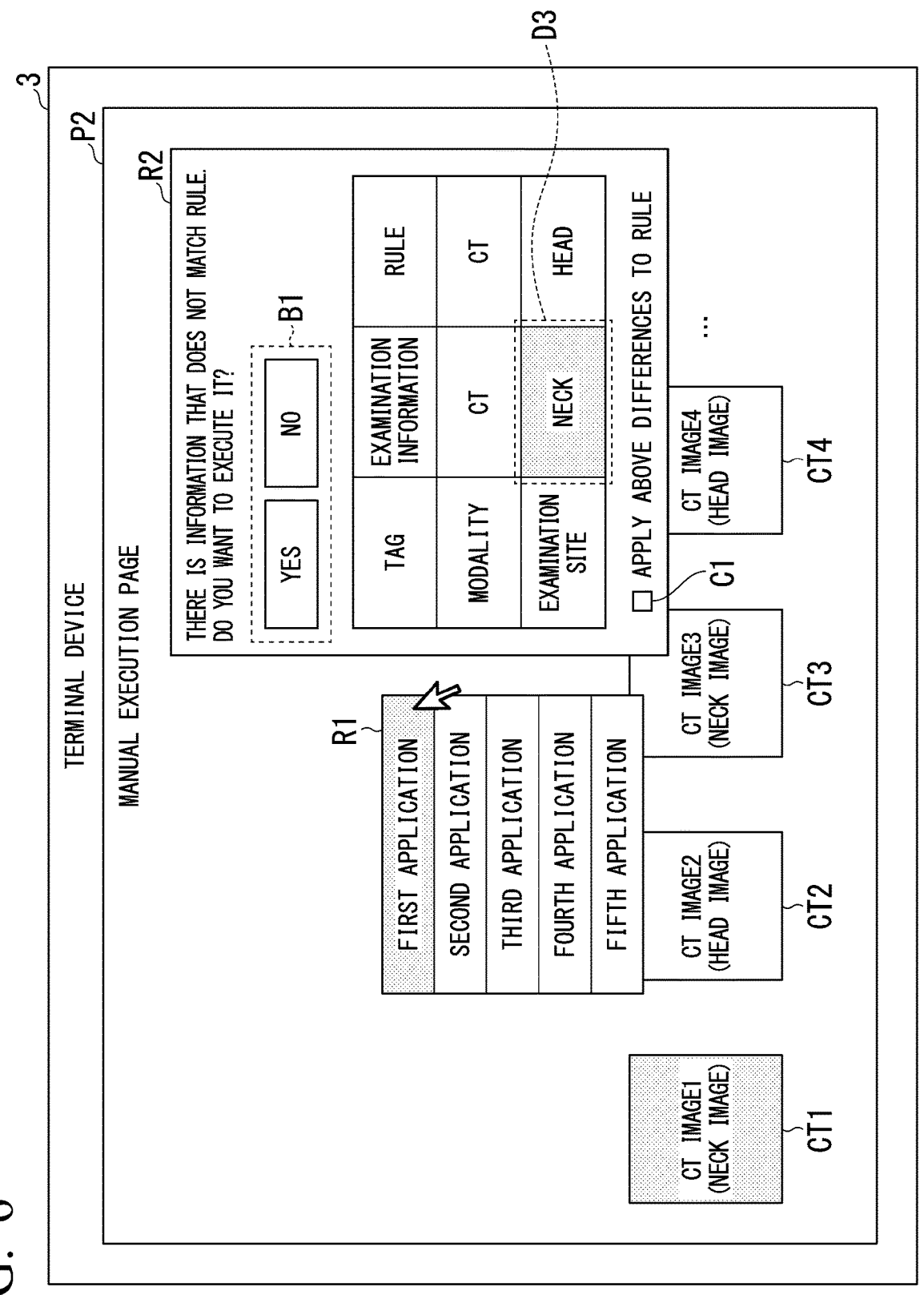
FIG. 6 is a diagram showing an example of a manual executed page P2 according to the embodiment.

FIG. 6 is a diagram showing an example of a manual execution page P2 displayed on the terminal device 3. In the example shown in FIG. 6, a "CT image (neck image) CT1" is selected as a medical image to be analyzed, and the "first application is selected as an application to be executed on the medical image from an application candidate list displayed in an area R1. The terminal device 3 transmits the medical image and application selection information to the medical information processing device 1.

Next, the comparison function 103 compares examination information of the selected medical image with tag setting information predetermined in the rule RL, and determines whether or not the examination information and the tag setting information match (step S207). If the comparison function 103 determines that both match (step S207; YES), the manual execution function 102-2 executes the selected application (step S217). Then, the display control function 104 generates information on a page displaying the execution result of the application and outputs the information to the terminal device 3.

On the other hand, if the comparison function 103 determines that both do not match (step S207; NO), the display control function 104 generates confirmation display (confirmation page) information for confirming execution of the application by the doctor or the like and outputs the information to the terminal device 3 (step S209). The terminal device 3 displays a confirmation display R2 on the basis of the received information. In the example shown in FIG. 6, a part D3 corresponding to the "examination site" tag, which is a difference between examination information of the medical image and the tag setting information predetermined in the rule RL, is highlighted with respect to the first application in the confirmation display R2. In addition, a question of "There is information that does not match the rule. Do you want to execute it?" and a button B1 for receiving a final execution instruction (first instruction) for the application are displayed in the confirmation display R2.

The doctor or the like can instruct execution/non-execution of the application by pressing the button B1 of either "yes" or "no" upon checking the content of the confirmation display R2. The terminal device 3 transmits the instruction of execution/non-execution of the application to the medical information processing device 1.

The button B1 is an example of a "first reception part." That is, the comparison function 103 determines whether or not the first information of the application manually designated by the user matches the second information of the medical image, and if it is determined that the first information and the second information do not match, the display control function 104 causes the display to display the confirmation page including the first reception part for receiving the first instruction as to whether or not to execute the application manually designated by the user.

In the example shown in FIG. 6, a check box C1 for receiving an instruction (second instruction) as to whether or not to apply settings of examination information of the medical image to the rule RL is displayed in the confirmation display R2. The doctor or the like can instruct application to the rule RL by checking the check box C1. When the application is instructed, the rule RL is updated. Processing of updating the rule RL will be described later. The terminal device 3 transmits the instruction of application/non-application to the rule RL to the medical information processing device 1.

The check box C1 is an example of a "second reception part." That is, the display control function 104 causes the display to display the confirmation page including the second reception part for receiving the second instruction as to whether or not to apply the content of the second information to the first information in addition to the first reception part.

Meanwhile, when the medical image to be analyzed is not normal data, such as data that has been received from another hospital or the like (which has a tag of "information on a facility where the apparatus is located" indicates a hospital or the like that is different from the hospital that manages the medical information processing device 1), the check box C1 for receiving the instruction of application/non-application to the rule RL may not be displayed. That is, the display control function 104 may not include the second reception part in the confirmation page when the imaging condition indicated by the second information is not a predetermined condition.

Referring back to FIG. 5, when the manual execution function 102-2 receives an instruction not to execute the application from the terminal device 3 (step S211; NO), the manual execution function ends processing of this flowchart without executing the application.

On the other hand, when the manual execution function 102-2 receives an instruction to execute the application from the terminal device 3 (step S211; YES), the manual execution function determines whether or not an instruction to apply to the rule RL has been received (step S213). If the manual execution function 102-2 determines that an instruction to apply to the rule RL has not been received (step S213; NO), the manual execution function executes the selected application (step S217). Then, the display control function 104 generates page information indicating a result of execution of the application and outputs the page information to the terminal device 3.

On the other hand, if the manual execution function 102-2 determines that an instruction to apply to the rule RL has been received (step S213; YES), an execution history including examination information of the medical image that is a target on which the application is executed is registered in the history information H stored in the memory 140 (step S215). Next, the manual execution function 102-2 executes the selected application (step S217). Then, the display control function 104 generates page information indicating a result of execution of the application and outputs the page information to the terminal device 3. Accordingly, processing of this flowchart ends.

(Rule Update Processing)

Figure 7:
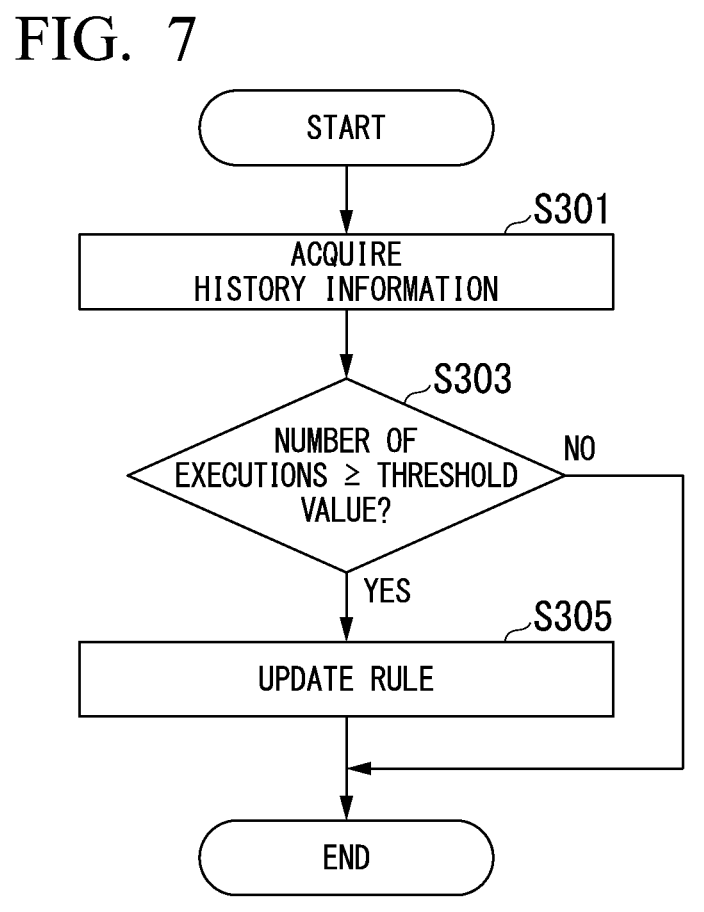

Next, rule update processing of the medical information processing device 1 will be described. FIG. 7 is a flowchart showing an example of a flow of rule update processing of the medical information processing device 1. The rule update processing shown in FIG. 7 is executed, for example, by batch processing every predetermined period (for example, every day). Alternatively, the rule update processing may be executed, for example, in response to an execution instruction from the operator of the medical information processing device 1 via the input interface 120. In this example, it is assumed that a plurality of execution histories to be applied to the rule RL are registered in the history information H stored in the memory 140 on the basis of an instruction from the doctor or the like.

First, the update function 105 acquires history information H from the memory 140 (step S301). Next, the update function 105 counts the number of executions for each setting of examination information of a medical image that is a target for execution of an application on the basis of execution histories included in the history information H, and determines whether or not the number of executions is equal to or greater than a predetermined threshold value (step S303). For example, if the number of executions of the first application with respect to settings of examination information of a medical image ("CT" for the "modality" tag and "NECK" for the "examination site" tag) is equal to or greater than the predetermined threshold value (for example, 3 times or the like) in the history information H, it can be determined that there is no problem even if the settings of the examination information of the medial image is applied as conditions (rule) for subsequent automatic execution. On the other hand, if the number of executions of the first application is less than the predetermined threshold value, there is a possibility that the first application has been manually executed exceptionally, and thus it is determined that the settings are not applied as conditions (rule) for automatic execution.

If the update function 105 determines that the number of executions is equal to or greater than the threshold value (step S303; YES), the update function 105 updates the rule (step S305). FIG. 8 is a diagram showing an example of a data configuration after updating the rule RL. In the updated rule RL shown in FIG. 8, the set value of the "examination site" tag of the "first application" has been updated to "HEAD/NECK" as a result of the update processing by the update function 105 as compared to the rule RL shown in FIG. 2. Thereafter, in processing of the automatic execution function 102-1 using this updated rule RL, the first application is automatically executed for a medical image of "NECK" as well in addition to the medical image for which the set value of the "examination site" tag of the "first application" is "HEAD."

That is, when the number of times the second instruction is received is equal to or greater than a predetermined threshold value, the update function 105 applies the content of the second information to the first information to update reference information.

On the other hand, if the update function 105 determines that the number of executions is not equal to or greater than the threshold value (step S303; NO), it does not update the rule RL. Accordingly, the processing of this flowchart ends. The update function 105 may have a function of deleting a part of the set rule. For example, the update function 105 may delete "NECK" added as a set value of the "examination site" tag of the "first application" by the update processing as described above according to an instruction of the user.

According to at least one embodiment described above, it is possible to provide information related to execution of an application by including the executor that automatically selects and executes an application to be executed on a medical image to be processed from among a plurality of applications on the basis of predetermined reference information, the comparator that compares first information indicating execution conditions for each of the plurality of applications included in the reference information with second information indicating imaging conditions for the medical image, and the display controller that causes the display to display a list of applications that have not been executed among the plurality of applications and a result of comparison between the first information and the second information.

Some or all of the functions of the medical information processing device 1 described above may be realized in the terminal device 3. In this case, the terminal device 3 is an example of a "medical information processing device."

The embodiment described above can be represented as follows.

A medical information processing device including processing circuitry, wherein the processing circuitry is configured to:

automatically select and execute an application to be executed on a medical image to be processed from among a plurality of applications on the basis of predetermined reference information;

compare first information indicating execution conditions for each of the plurality of applications included in the reference information with second information indicating an imaging condition for the medical image; and cause a display to display a list of applications that have not been executed among the plurality of applications and a result of comparison between the first information and the second information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing device, comprising:

processing circuitry configured to:

automatically select and execute an application to be executed on a medical image to be processed from among a plurality of applications based on predetermined reference information;

compare first information indicating execution conditions for each of the plurality of applications included in the reference information with second information indicating an imaging condition for the medical image; and cause a display to display a list of applications that have not been executed among the plurality of applications and a result of comparison between the first information and the second information, wherein the processing circuitry is further configured to execute an application manually designated by a user on the medical image;

determine whether the first information of the application manually designated by the user matches the second information of the medical image; and cause the display to display a confirmation page including a first reception part for receiving a first instruction as to whether or not to execute the application manually designated by the user, when it is determined that the first information and the second information do not match.

2. The medical information processing device according to claim 1, wherein the processing circuitry is further configured to cause the display to display a reason why the unexecuted applications have not been executed.

3. The medical information processing device according to claim 1, wherein the processing circuitry is further configured to cause the display to display information indicating a difference between the first information and the second information.

4. The medical information processing device according to claim 1, wherein the processing circuitry is further configured to cause the display to display the confirmation page including a second reception part for receiving a second instruction as to whether or not to apply content of the second information to the first information in addition to the first reception part.

5. The medical information processing device according to claim 4, wherein the processing circuitry is further configured to exclude the second reception part from the confirmation page when the imaging condition indicated by the second information is not a predetermined condition.

6. The medical information processing device according to claim 4, wherein the processing circuitry is further configured to update the reference information by applying the content of the second information to the first information when a number of times the second instruction is received is equal to or greater than a predetermined threshold value.

7. A medical information processing method, using a computer of a medical information processing device, comprising:

automatically selecting and executing an application to be executed on a medical image to be processed from among a plurality of applications based on predetermined reference information;

comparing first information indicating execution conditions for each of the plurality of applications included in the reference information with second information indicating an imaging condition for the medical image; and causing a display to display a list of applications that have not been executed among the plurality of applications and a result of comparison between the first information and the second information, wherein the medical information processing method further comprises executing an application manually designated by a user on the medical image;

determining whether the first information of the application manually designated by the user matches the second information of the medical image; and causing the display to display a confirmation page including a first reception part for receiving a first instruction as to whether or not to execute the application manually designated by the user, when it is determined that the first information and the second information do not match.

8. A non-transitory computer-readable storage medium storing a program causing a computer of a medical information processing device to:

automatically select and execute an application to be executed on a medical image to be processed from among a plurality of applications based on predetermined reference information;

compare first information indicating execution conditions for each of the plurality of applications included in the reference information with second information indicating an imaging condition for the medical image; and cause a display to display a list of applications that have not been executed among the plurality of applications and a result of comparison between the first information and the second information, wherein the program further causes the computer of the medical information processing device to execute an application manually designated by a user on the medical image;

determine whether the first information of the application manually designated by the user matches the second information of the medical image; and cause the display to display a confirmation page including a first reception part for receiving a first instruction as to whether or not to execute the application manually designated by the user, when it is determined that the first information and the second information do not match.

\* \* \* \* \*